United States Patent [19]

Pugin

[11] Patent Number: 5,777,062
[45] Date of Patent: Jul. 7, 1998

[54] DIPHOSPHINES BONDED TO SIDE CHAINS OF POLYMERS, AND METAL COMPLEXES THEREOF

[75] Inventor: Benoit Pugin, Münchenstein, Switzerland

[73] Assignee: Novartis Corporation, Summit, N.J.

[21] Appl. No.: 606,158

[22] Filed: Feb. 23, 1996

[51] Int. Cl.⁶ .................................................. C08G 18/28
[52] U.S. Cl. ................................. 528/72; 528/53; 528/62
[58] Field of Search ................................. 528/53, 62, 72

[56] References Cited

U.S. PATENT DOCUMENTS

| | | | |
|---|---|---|---|
| 4,879,389 | 11/1989 | Achiwa. | |
| 4,923,996 | 5/1990 | Muller et al. | |
| 4,994,615 | 2/1991 | Spindler et al. | 564/304 |
| 5,043,474 | 8/1991 | Müller et al. | 562/15 |
| 5,244,857 | 9/1993 | Pugin et al. | 502/167 |
| 5,252,751 | 10/1993 | Pugin et al. | 549/214 |

OTHER PUBLICATIONS

K. Iichiwa discussed in, J. Chem. Japan, Soc., Chemistry Letters, pp. 905–908 (1978).

K. J. Sitlle, J. Macromol. Sci Chem A21 (13 & 14), 1984, pp. 1689–1693.

A. Börner et al., Tetrahedron Lett. 35(33), 1994, 6071.

A. Börner et al., Tetrahedron Lett., 50(35), 1994, pp. 10419–10430.

Van Den Berg et al., J. of Molecular Catal., 51 pp. 13–27 (1989).

J. M. Frechet et al., Polymer, 20, pp. 675–680 (1979).

*Primary Examiner*—John M. Cooney, Jr.
*Attorney, Agent, or Firm*—William A. Teoli, Jr.

[57] ABSTRACT

The invention relates to polymers having structural repeating units of at least one monomer MM which contains a hydroxyl group or a primary or secondary amine group as a functional group bonded directly or in a side chain, wherein the functional group is bonded via a bridge group Q formed by a diisocyanate to the hydroxyl group or primary or secondary amino group of an aliphatic, cycloaliphatic, heterocycloaliphatic, aromatic or heteroaromatic ditertiary diphosphine, the phosphine groups of which are bonded to a carbon chain in the 1,2-, 1,3-, 1,4- or 1,5-position relative to one another. The invention also relates to a process for their preparation and to rhodium and iridium complexes with these diphosphine ligands. Using these rhodium and iridium complexes, optically pure compounds which are valuable intermediates for the preparation of biologically active ingredients, in particular in the field of pharmaceuticals and agrochemicals, can be obtained in a hydrogenation process which is likewise according to the invention. Thus, for example, it is possible to prepare from secondary amines, in particular N-carbalkoxymethylamines, 5-imidazolecarboxylic acid derivatives which have a herbicidal action and can be used for weed control (EP-A-0 207 563). The optically pure (α-aminocarboxylic acid esters are suitable for peptide syntheses.

After the hydrogenation, the catalysts can easily be separated off, if appropriate purified and re-used.

31 Claims, No Drawings

DIPHOSPHINES BONDED TO SIDE CHAINS OF POLYMERS, AND METAL COMPLEXES THEREOF

The invention relates to diphosphines which are bonded to side chains of polymers, metal complexes thereof with rhodium or iridium, and the use of these complexes for hydrogenation of double bonds and triple bonds in organic compounds, in particular for enantioselective hydrogenation of prochiral organic compounds using corresponding immobilized chiral diphosphines.

EP-A-0 256 982 describes enantioselective hydrogenation of ketimines to give optically active secondary amines with the aid of chiral dioxolane-iridiumdiphosphine complexes as homogeneous catalysts. However, the expensive catalysts cannot be recovered or can be recovered only using expensive separation methods, which is always associated with undesirable losses. Furthermore, these catalysts often suffer a high loss of activity in the course of the first reaction, so that re-use is not possible. There is therefore a need for catalysts which are easy to separate off and can be re-used, the activity and in particular the selectivity of which is largely retained during repeated use.

EP-A-0-496 699 and EP-A-0 496 700 proposes dioxolane- and pyrrolidine-diphosphines containing silane groups and rhodium or iridium complexes thereof, which are fixed to an inorganic support material, for example silicates. In this manner, a heterogeneous reaction solution is obtained during the hydrogenation, from which the inorganically fixed catalyst can easily be separated off after the reaction has ended. This process cannot be completely satisfactory for the following reasons: a) the hydrogenation reaction proceeds heterogeneously in all cases, and b) relatively large amounts of support material must be employed, since the inorganic support materials can be coated with only small amounts of the catalytically active compounds.

On the other hand, polymeric support materials in which the diphosphine component is on a copolymeritable unit which is then copolymerized together with other monomers, so that the diphosphine or its metal complex is bonded directly in the polymer chain, have also been disclosed.

K. Achiwa in J. Chem. Japan. Soc., Chemistry Letters, pages 905 to 908 (1978) describes polystyrene copolymers, the benzene radicals of which contain pyrrolidine-diphosphine-N-carbonyl groups complexed with rhodium. The synthesis of the monomers is difficult and the hydrogenation of prochiral olefins with these heterogeneous catalysts is associated with a reduction in activity and in enantioselectivity, compared with catalysts which are not bonded to a polymer. The pyrrolidine-diphosphine ligands are fixed via a para-amide bond directly to the benzene radical of the styrene which forms one part of the copolymer, while the other part of the copolymer skeleton by hydroxyethyl methacrylate. The mobility of the diphosphine ligands is severely limited by this direct bond to the polymer base skeleton.

Another disadvantage of this fixing concept is that the polymer must be built up again, which is expensive and leads to properties which are not exactly foreseeable in respect of solubility in organic solvents, ease of separation or ease of precipitation after the hydrogenation reaction. Such a polymer build-up promotes partial inclusion of the catalytically active part and thus leads to a reduced activity and productivity.

In view of these disadvantages, it seems desirable to start from polymers having known properties and to modify these with catalytically active compounds so that the polymer properties are changed only slightly and no inclusions or other changes occur on the catalytically active part of the compounds.

Nevertheless, the principle described above of fixing by copolymerization of catalytically active units is given preference over subsequent modification of an existing polymer. K. J. Stille in J. Macromol. Sci.-Chem. A21 (13 & 14), 1984, 1689–1693, thus reports that a large number of unsuitable catalysts which show poor overall yields in the hydrogenation and poor enantioselectivities have been obtained by the route of subsequent modification of, for example, polystyrene beads.

In EP-A-0 329 043, a water-soluble rhodium-catalyst is prepared by bonding oligomeric or low molecular weight polymeric polyethylene oxides, of which the structural element repetition is between 5 and 1000, to 3,4-bis(diarylphosphino)-pyrrolidine. For this, the terminal hydroxyl groups are reacted with an isocyanate group of an aliphatic or aromatic diisocyanate and the still free isocyanate group is bonded with 3,4-bis(diarylphosphino) pyrrolidine. Water-soluble catalysts for asymmetric hydrogenation of olefins are obtained by complexing with Rh. Since in each case only the end groups of the oligomeric or polymeric ethylene oxides are functionalized with OH groups, only little diphosphine ligand can be bonded per polymer unit, or oligomeric units of very low molecular weight must be present, but these can then no longer be separated off easily from the reaction mixture.

It has now been found, surprisingly, that very active polymer-bonded catalysts of diphosphines and metal complexes thereof can be prepared if the starting substances used are polymeric base matrices containing hydroxyl, primary amine or secondary amine functional groups, some or all of the functional groups of which are bonded to a diisocyanate providing distance from the polymer chain, to form a urethane or urea bridge, the second isocyanate group of which is bonded to an aliphatic, cycloaliphatic, heterocycloaliphatic, aromatic or heteroaromatic 1,2-, 1,3-, 1,4- or 1,5-diphosphine which likewise contains a hydroxyl, primary amine or secondary amine group. The mobility and accessibility of the ligand can be adjusted by choosing the nature and length of the diisocyanate. In particular, dioxolane-diphosphines or pyrrolidine-diphosphines bonded in this way lead to valuable catalysts for hydrogenations, especially for enantioselective hydrogenations.

The preparation of these polymer-bonded diphosphines is particularly simple and starts from polymers having known properties, which, for example, are reacted with a diisocyanate in a first step.

In a second step, the remaining isocyanate groups can be reacted with the diphosphine containing hydroxyl, primary amine or secondary amine groups. If this second step is only partly carried out, the residual isocyanate content can be used for subsequent crosslinking by reaction with a polyalkylene glycol, a diol or a diamine.

Further modification of the polymer is also possible by further reacting the residual isocyanate groups, for example with an alkylene glycol or polyalkylene glycol etherified on one side, an alcohol or an amine. Even subsequently after introduction of the diphosphine group, the polymer properties can be modified again in a controlled manner in this way. Considerably more possibilities for adaptation of the catalysts to the reaction medium than with known processes are obtained in this manner, which offers significant advantages on a large industrial scale in particular. The two process variants can also be combined.

The metal complexes of rhodium or iridium prepared therefrom have a high selectivity in asymmetric hydrogenations, and their catalyst activity is considerably higher than that of previously known catalysts immobilized on polymers.

The reaction to be catalysed can be conducted heterogeneously or homogeneously by choosing the polymer. The polymer can be chosen and also subsequently modified such that the catalyst can easily be separated off and re-used after the reaction. The catalysts can be re-used several times, and any losses in activity can be compensated by addition of small amounts of fresh catalyst. By choosing the polymer, the catalyst can be adapted to the optimum to the reaction medium during the hydrogenation step and then separated off completely, which is of particular importance for hydrogenations carried out on a large industrial scale. Furthermore, the recovery of the noble metals contained in the catalyst is made easier if the catalyst has to be changed after frequent recycling. Purification of the hydrogenated end product is also made considerably easier by this procedure.

The invention relates to polymers having recurring structural elements of at least one monomer MM which contains a hydroxyl group or a primary or secondary amine group as a functional group bonded directly or in a side chain, wherein the functional group is bonded via a bridge group Q formed by a diisocyanate to the hydroxyl group or primary or secondary amino group of an aliphatic, cycloaliphatic, heterocycloaliphatic, aromatic or heteroaromatic ditertiary diphosphine, the phosphine groups of which are bonded to a carbon chain in the 1,2-, 1,3-, 1,4- or 1,5-position relative to one another.

The choice of diisocyanate is not critical per se. In particular the bridge group Q can be formed by at least 3 C-atoms. Diisocyanates which are suitable and available on a large industrial scale are described, for example, in Houben Weyl, Makromolekulare Stoffe |macromolecular substances|, Volume E 20, pages 1587 to 1593, 1987 edition.

Preferred diisocyanates are those in which the bridge group Q is formed by a linear or branched aliphatic $C_2$–$C_{20}$alkyl which is unsubstituted or mono- or polysubstituted by $C_1$–$C_6$ alkyl or $C_1$–$C_6$alkoxy, $C_3$–$C_8$cycloalkyl or heterocycloalkyl which is unsubstituted or mono- or polysubstituted by $C_1$–$C_6$alkyl or $C_1$–$C_6$alkoxy, linear or branched aliphatic $C_2$–$C_{20}$alkyl which is interrupted by unsubstituted or $C_1$–$C_6$alkyl- or $C_1$–$C_6$alkoxy-substituted $C_3$–$C_8$cycloalkyl or heterocycloalkyl and is unsubstituted or substituted by $C_1$–$C_6$alkyl or $C_1$–$C_6$alkoxy, phenyl, naphthyl, biphenyl or $C_3$–$C_{10}$heteroaryl which is unsubstituted or mono- or polysubstituted by $C_1$–$C_6$alkyl or $C_1$–$C_6$alkoxy, or linear or branched aliphatic $C_2$–$C_{20}$alkyl which is interrupted by phenyl, naphthyl or $C_3$–$C_{10}$heteroaryl and is unsubstituted or substituted by $C_1$–$C_6$alkyl or $C_1$–$C_6$alkoxy The linear or branched $C_1$–$C_{20}$alkyl radicals are, for example, methyl, ethyl and the various position isomers of propyl, butyl, pentyl, hexyl, heptyl, octyl, nonyl, decyl, undecyl, dodecyl, tridecyl, tetradecyl, pentadecyl or hexadecyl, heptadecyl, octadecyl, nonadecyl or eicosyl.

The $C_1$–$C_6$alkoxy radicals can be linear or branched and are, for example, methoxy, ethoxy and the various positional isomers of propoxy, butoxy, pentoxy or hexoxy.

Heterocycloalkyl is, for example, pyrrolidine, piperidine, morpholine, oxazolidine, dioxolane, or an isocyanuric acid triester group.

$C_3$–$C_8$cycloalkyl is, for example, cyclopropyl, dimethylcyclopropyl, cyclobutyl, cyclopentyl, methylcyclopentyl, cyclohexyl, cycloheptyl or cyclooctyl.

Aromatic means, for example, phenyl, naphthyl or anthracenyl.

Heteroaromatic means, for example, pyridine, pyrimidine, pyrrole, furan, imidazole, pyrazole or triazine.

Particularly preferred diisocyanates are 1,6-bis|isocyanato|hexane, 5-isocyanato-3-(isocyanatomethyl)-1,1,3-trimethylcyclohexane, 1,3-bis|5-isocyanato-1,3,3-trimethyl-phenyl|-2,4-dioxo-1,3-diazetidine, 3,6-bis|9-isocyanatononyl|-4,5-di(1-heptenyl)cyclohexene, bis|4-isocyanatocyclohexyl|methane, trans-1,4-bis|isocyanato|cyclohexane, 1,3-bis|isocyanatomethyl|benzene, 1,3-bis|1-isocyanato-1-methylethyl|benzene, 1,4-bis|2-isocyanatoethyl|cyclohexane, 1,3-bis|isocyanatomethyl|cyclohexane, 1,4-bis|1-isocyanato-1-methylethyl|benzene, bis|isocyanato|isododecylbenzene,1,4-bis|isocyanato|benzene, 2,4-bis|isocyanato|toluene, 2,6-bis|isocyanato|toluene, 2,4-/2,6-bis|isocyanato|toluene, 2-ethyl-1,2,3-tris|3-isocyanato-4-methylanilinocarbonyloxy|propane, N,N'-bis|3-isocyanato-4-methylphenyl|urea, 1,4-bis|3-isocyanato-4-methylphenyl|-2,4-dioxo-1,3-diazetidine, 1,3,5-tris|3-isocyanato-4-methylphenyl|-2,4,6-trioxohexahydro-1,3,5-triazine, 1,3-bis|3-isocyanato-4-methylphenyl|-2,4,5-trioxoimidazolidine, bis|2-isocyanatophenyl|methane, (2-isocyanatophenyl)(4-isocyanato-phenyl)methane, bis|4-isocyanatophenyl|methane, 2,4-bis|4-isocyanatobenzyl|-1-isocyanatobenzene, |4-isocyanato-3-(4-isocyanatobenzyl)-phenyl||2-isocyanato-5-(4-isocyanatobenzyl)phenyl|methane, tris|4-isocyanatophenyl|methane, 1,5-bis|isocyanato|naphthalene, or 4,4'-bis|isocyanato|-3,3'-dimethylbiphenyl.

Especially preferred diisocyanates are 1,6-bis|isocyanato|hexane, 5-isocyanato-3-(isocyanatomethyl)-1,1,3-trimethylcyclohexane, 2,4-bis|isocyanato|toluene, 2,6-bis|isocyanato|toluene, 2,4-/2,6-bis|isocyanato|toluene or bis|4-isocyanatophenyl|methane.

Hydroxyl- and amino-functionalized diphosphines which form complexes with transition metals and can be employed for catalytic hydrogenations, in particular for enantioselective catalytic hydrogenation, are known or can be prepared by analogous processes. Examples are described in the Handbook of Enantioselective Catalysis, Volume 2, Ed. H. Brunner, W. Zettlmeier, VCH Verlag Weinheim 1993.

Preferred diphosphines are polymers in which the tertiary phosphine groups in the 1,2-, 1,3-, 1,4- or 1,5-position are bonded to an aliphatic radical having a total of 4 to 12 C atoms, a cycloaliphatic radical having 3 to 8 C atoms, a heterocycloaliphatic radical having 2–6 C atoms in the heterocyclic moiety, an aromatic radical having 6 to 20 C atoms or a heteroaromatic radical having 2 to 12 C atoms in the heterocyclic moiety.

The aliphatic diphosphines can be phosphine radicals bonded to $C_4$–$C_{12}$alkyl, the alkyl skeleton of which contains a hydroxyl or amino group bonded directly or in a side chain.

The cycloaliphatic diphosphines can be derived from cyclopropyl, cyclopentyl or cyclohexyl. However, the bridges can also be bicyclic, for example bicycloheptane or bicyclooctane, which can contain a directly bonded hydroxyl or amino group.

Heterocyclic diphosphines can be, for example, derivatives of dioxolane, pyrrolidine or piperidine.

Aromatic diphosphines can be derived, for example, from phenyl, biphenyl, naphthyl or binaphthyl.

Suitable diphosphines are, for example, those of the formula 100, 101, 102, 103, 104, 105, 106, 107, 108, 109 and 110.

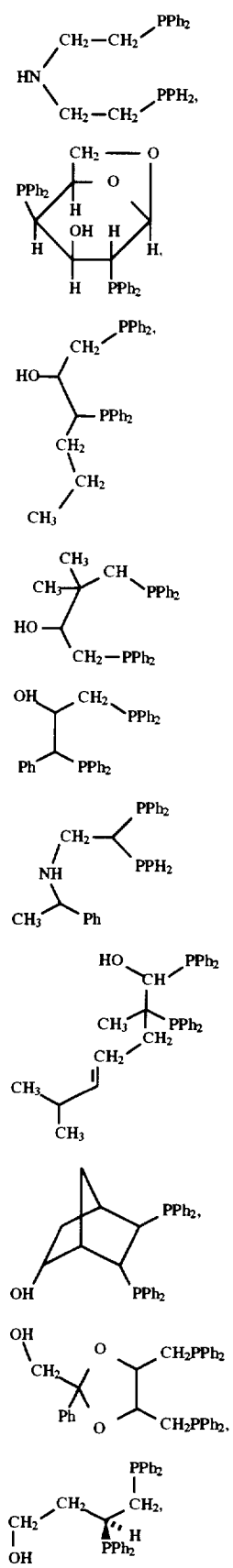

(100)

$$\underset{CH_3}{\overset{PPh_2}{\underset{|}{CH}}}\underset{CH_2}{\overset{}{\phantom{X}}}\underset{CCH}{\overset{PPh_2}{\underset{\vdots}{\phantom{X}}}}\underset{CH_2}{\overset{}{\phantom{X}}}\underset{CH_2}{\overset{}{\phantom{X}}}OH.$$ (110)

The diphosphines of the formula 100 to 107 are known and are described in Handbook of Enantioselective Catalysis. Volume 2. Editors H. Brunner. W. Zettlmeier. VCH Verlag Weinheim 1993. The compound of the formula 108 is likewise known and is described by A. Borner et al., Tetrahedron Lett. 35, 1994, 6071, the compound of the formula 109 is known and is described in Tetrahedron 1994, 50(35), 10419–30, and the compound of the formula 110 can be prepared in a manner analogous to this.

The following primary amino-functional compounds of the formula Ia are likewise known and their preparation is described in EP-A-496 700. The secondary amines can be obtained from these in a simple manner by known alkylation processes.

The compounds of the formula Ib are likewise known from EP-A-496 699, and their preparation is described there.

A preferred group of polymers is derived from diphosphines of the formula Ia or Ib.

(Ia)

(Ib)

in which the $R_1$ are identical or different radicals and independently of one another are $C_1$-$C_1$-$C_{12}$alkyl, $C_5$-$C_{12}$cycloalkyl, phenyl, $C_5$-$C_{12}$cycloalkyl which is substituted by $C_1$-$C_4$alkyl or $C_1$-$C_4$alkoxy or phenyl which is mono- to trisubstituted by $C_1$-$C_4$alkyl, $C_1$-$C_4$alkoxy, $C_1$-$C_4$halogenalkyl, —$SiR_4R_5R_6$, halogen, —$SO_3M$, —$CO_2M$, —$PO_3M$, —$NR_7R_8$ or —[$^+NR_7R_8R_9$]$X^-$;

or the two $R_1$ of a group $(R_1)_2P$ together are o,o'-diphenylene;

$R_2$ is hydrogen, linear or branched $C_1$-$C_{12}$alkyl, phenyl or benzyl;

$R_3$ is $C_1$-$C_{12}$alkylene;

the groups $(R_1)_2P(CH_2)_{m\ or\ n}$ are in the o- or m-position relative to one another;

B is —$NR_{10}$- or —O—;

$R_4$, $R_5$ and $R_6$ independently of one another are $C_1$-$C_{12}$alkyl or phenyl;

$R_7$ and $R_8$ are H, $C_1$-$C_{12}$alkyl or phenyl, or $R_7$ and $R_8$ together are tetramethylene, pentamethylene or 3-oxa-1,5-pentylene;

$R_9$ is H or $C_1$-$C_4$alkyl;

M is H or an alkali metal;

$X^-$ is the anion of a monobasic acid;

$R_{10}$ is hydrogen or linear or branched $C_1$-$C_6$alkyl;

and m and n independently of one another are 0 or 1.

The alkyl $R_1$ can be linear or branched and preferably contain 1 to 8, particularly preferably 1 to 4 C atoms. Examples of this alkyl are methyl, ethyl, n- and i-propyl, n-, i- and t-butyl, pentyl, hexyl, heptyl, octyl, nonyl, decyl, undecyl and dodecyl. Methyl, ethyl, n- and i-propyl and n-, i- and t-butyl are preferred.

The cycloalkyl $R_1$ preferably contain 5 to 8, particularly preferably 5 or 6 ring C atoms. Examples of cycloalkyl are cyclopentyl, cyclohexyl, cycloheptyl, cyclooctyl, cyclodecyl and cyclododecyl. Cyclopentyl and cyclohexyl are preferred and cyclohexyl is particularly preferred.

The cycloalkyl can be substituted, for example by 1 to 3 alkyl or alkoxy substituents. Examples of such substituents have been given above. Preferred substituents are methyl and ethyl, and methoxy and ethoxy. Examples of substituted cycloalkyl are methyl- and methoxycyclopentyl and -cyclohexyl.

Substituted phenyl $R_1$ preferably contains 1 or 2 substituents. If the phenyl contains 2 or 3 substituents, these can be identical or different. Examples of the alkyl and alkoxy substituents have been given above; preferred alkyl and alkoxy substituents for phenyl are methyl, ethyl and methoxy and ethoxy.

If the substituent on the phenyl is halogen, it is preferably —F, —Cl or —Br.

$R_4$, $R_5$ and $R_6$ can be linear or branched alkyl, which preferably contains 1 to 8 and particularly preferably 1 to 4 C atoms. Examples of alkyl have been given above. Preferred alkyl is methyl, ethyl, n-propyl, n-butyl and t-butyl. The substituent —$SiR_4R_5R_6$ is particularly preferably trimethylsilyl.

Of the acid substituents —$SO_3M$, —$CO_2M$ and —$PO_3M$ on the phenyl, the —$SO_3M$ group is preferred. M is preferably H, Li, Na or K.

Alkyl $R_7$ and $R_8$ preferably contain 1 to 6, particularly preferably 1 to 4 C atoms. The alkyl is preferably linear. Preferred examples are methyl, ethyl, n-propyl and n-butyl. Alkyl $R_9$ is preferably methyl.

An anion $X^-$ of a monobasic acid is preferably $Cl^-$, $Br^-$ or the anion of a carboxylic acid, for example formate, acetate, trichloroacetate or trifluoroacetate.

Some preferred examples of substituted phenyl are 2-methyl-, 3-methyl-, 4-methyl-, 2- or 4-ethyl-, 2- or 4-i-propyl-, 2- or 4-t-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-$SO_3H$-, 2- or 4-$SO_3Na$-, 2- or 4-[$^+NH_3Cl$]-, 3,4,5-trimethylphen-1-yl, 2,4,6-trimethylphen-1-yl, 4-trifluoromethylphenyl or 3,5-di(trifluoromethyl).

A preferred sub-group of polymers is obtained if the $R_1$ in formula Ia or Ib are identical radicals and are phenyl, cyclohexyl, t-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1-yl, 4-trifluoromethylphenyl or 3, 5-di(trifluoromethyl).

Another particularly preferred sub-group of polymers is obtained if the $R_1$ in formula Ia or Ib are phenyl and m+n in formula Ib is 0, 1 or 2. Especially preferred polymers are those of the formula Ib in which $R_1$ is phenyl, m is 0 and n is 1 and the groups $(R_1)_2P$- and $(R_1)_2PCH_2$- are bonded in the m-position, or m and n are 0 and the groups $(R_1)_2P$- are bonded in the o-position.

The radicals of the formula Ia and Ib can be in the form of enantiomer mixtures. Polymers which contain the radicals of the formula Ia or Ib in the form of the optically active R,R-, S,S-, R,S- or S,R-isomers, with respect to the position of the phosphine(methyl) groups, are preferred.

The polymers according to the invention can be non-crosslinked thermoplastic, crosslinked or structurally crosslinked polymers.

The polymers can be either polymers of olefinically unsaturated monomers, for example polyolefins, polyacrylates, polyisoprenes, polybutadiene, polystyrene, polyphenylene, polyvinyl chloride, polyvinylidene chloride or polyallyl compounds, or they can be polyaddition compounds, for example polyurethanes or polyethers. Polycondensed products are polyesters or polyamides.

If the polymers are essentially non-crosslinked (thermoplastics), they can be polymers which are soluble in organic solvents. Partly crosslinked polymers are usually only swellable in organic solvents, and highly crosslinked polymers can be insoluble and advantageously porous materials.

Crosslinked polymers (thermosetting resins) can be phenol-aldehyde resins, for example in the form of Bakelites, urea- or melamine-formaldehyde resins, crosslinked polyurethane resins or crosslinked epoxy resins.

Suitable crosslinking components for epoxy resins are, in particular, di- or triamines. Crosslinked polymers based on triglycidyl isocyanurate are also possible.

Unsaturated polyester resins which are derived from copolyesters of saturated and unsaturated dicarboxylic acids with polyhydric alcohols, and vinyl compounds as crosslinking agents, are also examples of suitable polymers.

Crosslinkable acrylic resins which are derived from substituted acrylic acid esters, for example from epoxy acrylates, urethane acrylates or polyester acrylates are likewise possible.

Alkyd resins, polyester resins and acrylate resins which are crosslinked with melamine resins, urea resins, polyisocyanates or epoxy resins form another group.

Preferred crosslinked systems are those of olefinically unsaturated monomers. Examples are polyacrylates, polyolefins or polystyrene. The crosslinking component is also olefinically unsaturated. An example is polystyrene crosslinked with divinylbenzene.

Examples of linear polymers which are soluble in organic solvents are given below.

The polymers to be used according to the invention are known per se and in some cases are commercially obtainable, or they can be prepared by known polymerization processes or by subsequent modification of polymers.

The polymer preferably comprises the hydroxyl-, primary or secondary amino-functional monomer in an amount of 1 to 100 mol per cent, particularly preferably 5 to 100 mol per cent, especially 10 to 100 mol per cent, if the polymers are soluble or swellable polymers in which the functional group is already present.

The loading of the polymer via a diisocyanate bridge group with tertiary diphosphine groups in the 1,2-,1,3-,1,4- or 1,5-position is preferably between 5 and 100 mol %, particularly preferably between 5 and 50 mol %, based on the available hydroxyl or primary or secondary amino group of the polymer.

If the polymers are crosslinked polymers which are subsequently functionalized, preferably 1 to 50 mol per cent, particularly preferably 1 to 20 mol per cent, of hydroxyl- or primary or secondary amino-functional groups are present the mol per cent data relating to the monomer forming the majority of the polymer.

The monomers forming the polymer are preferably chosen from the group consisting of styrene, p-methylstyrene and α-methylstyrene, at least one of which contains a hydroxyl group or a primary or secondary amino group bonded as a functional group.

Further comonomers which form copolymers with styrene derivatives may be present, for example styrene p-methylstyrene or α-methylstyrene, butadiene, maleic anhydride, acrylate or methacrylates and ethylene, propylene or butylene. Copolymers of, for example, styrene/butadiene, styrene/acrylonitrile, styrene/alkyl methacrylate, styrene/butadiene/alkyl acrylate and methacrylate, styrene/maleic anhydride and styrene/acrylonitrile/methyl acrylate; mixtures of styrene copolymers and another polymer, for example a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene are then present.

Graft copolymers of styrene or α-methylstyrene, for example styrene on polybutadiene, styrene on polybutadiene-styrene or polybutadiene/acrylonitrile copolymers and styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates and styrene and acrylonitrile on acrylate/butadiene copolymers are also suitable.

The comonomers of diene or acrylic derivatives, for example butadiene, acrylonitrile, alkyl methacrylate, butadiene/alkyl acrylate and methacrylate, maleic anhydride and acrylonitrile/methyl acrylate, which form random or block copolymers are preferred.

Another preferred group of polymers is formed by monomers derived from α,β-unsaturated acids or esters or amides thereof, structural elements of which contain a hydroxyalkyl group or a primary or secondary aminoalkyl group bonded as a functional group in the ester or amide group.

Particularly preferred monomers are those from the group consisting of acrylates and $C_1-C_4$alkyl esters thereof, methacrylates and $C_1-C_4$alkyl esters thereof, acrylamide and acrylonitrile, structural elements of which contain a hydroxyl group or a primary or secondary amino group bonded as a functional group.

Other comonomers which form copolymers, are derived from olefinically unsaturated monomers and form random polymers or block copolymers can also be present. Suitable comonomers are acrylates and $C_1-C_4$alkyl esters thereof, methacrylates and $C_1-C_4$alkyl esters thereof, acrylamide and acrylonitrile and butadiene, vinyl chloride or vinyl fluoride.

Another group of preferrred polymers is formed by monomers which contain vinyl alcohol as a homopolymer or vinyl alcohol as a copolymer with vinyl acetate, stearate, benzoate or maleate, vinylbutyral, allylphthalate or allylmelamine.

Polymers which are also preferred are formed from phenol and a $C_1-C_4$aldehyde, particularly preferably from phenol and formaldehyde. The polymers are known as phenol-formaldehyde resins which are still soluble, in particular as novolaks, and are commercially obtainable.

Another preferred group of polymers is derived from bisglycidyl ethers and diols. These are hydroxyl-functional polyethers which are prepared, for example, from bisglycidyl ethers and bisphenol A.

The polyepoxides can be built up from diepoxide comonomers having preferably 6 to 40, and particularly preferably 8 to 30 C atoms and diols as comonomers having preferably 2 to 200, and particularly preferably 2 to 50 C atoms. A preferred group derived from these is formed from monomers which build up a polymer from cyclic $C_3-C_6$ethers or $C_2-C_6$alkylene glycols with bisglycidyl ethers. The bisglycidyl ethers can be aromatic, aliphatic or cycloaliphatic.

Other preferred polymers with hydroxyl groups as functional groups are derived from polysaccharides.

Partial cellulose acetates, propionates or butyrates, partial cellulose ethers, starch, chitin and chitosan are particularly preferred.

Other polymers are derived from polymers with reducible groups, for example nitrile groups, ketone groups, carboxylic acid esters and carboxylic acid amides.

Polymers which are insoluble in the reaction medium and are functionalized on the surface with hydroxyl or amino groups by a chemical or physical process can also be used. Examples of crosslinked polymers which are insoluble in organic solvents are given above. For example, partly unsaturated polymers can be provided with hydroxyl groups on the surface by oxidation, for example with hydrogen peroxide. Another possibility is plasma treatment in, for example, an oxygen atmosphere or a nitrogen or ammonia atmosphere. The polymers are preferably in the form of a powder. Among these support materials, polystyrene which is subsequently functionalized with hydroxyl, amino or hydroxymethyl groups is particularly preferred.

The polymers according to the invention are particularly preferably derived from recurring structural elements of at least one monomer MM of the formula IIa, IIb, IIc or IId

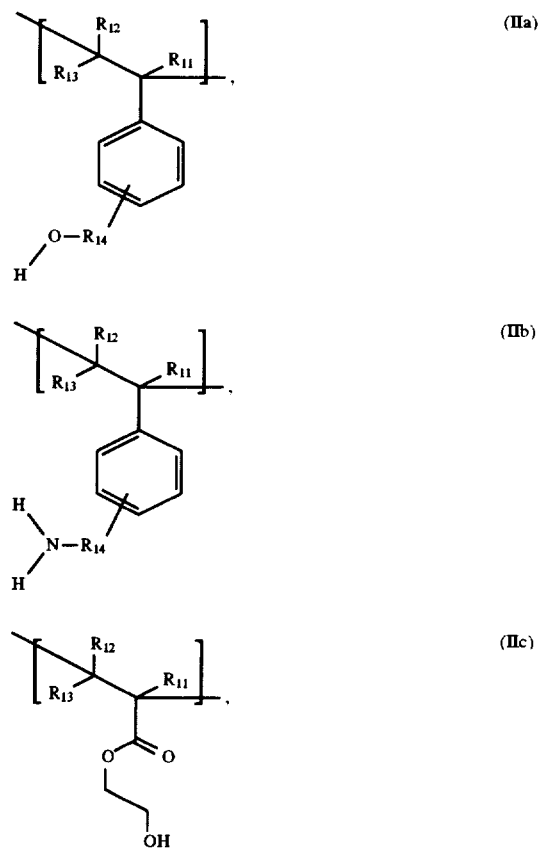

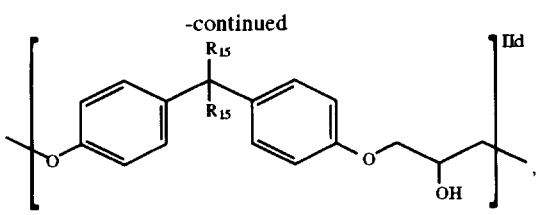

in which $R_{14}$ is $C_1$–$C_4$alkylene and $R_{11}$, $R_{12}$, $R_{13}$ and $R_{15}$ independently of one another are hydrogen or $C_1$–$C_4$alkyl.

The polymers preferably have an average molecular weight of 5 000 to 5 000 000 Dalton, and the molecular weight is particularly preferably 10 000 to 1 000 000 Dalton.

In the case of swellable polymers, these are preferably derived from polystyrene, polymethacrylate or polyacrylate, these preferably being between 0.5 mol per cent and 5 mol per cent crosslinked with an olefinically unsaturated compound.

Highly crosslinked polymers are preferably highly crosslinked macroporous polystyrene or polyacrylate which contains bonded recurring structural units of a monomer having a hydroxyl group or a primary or secondary amino group as the functional group. The particle size of the highly crosslinked polymers is preferably 10 μm to 2000 μm, particularly preferably 50 μm to 500 μm.

The specific surface area of porous highly crosslinked polymers is preferably 5 to 1000 m²/g, particularly preferably 50–500 m²/g, determined by the BET method.

The present invention also relates to a process for the preparation of the polymers according to the invention which are soluble, swellable or insoluble in organic solvents, which comprises reacting the polymers having recurring structural elements of at least one monomer MM which contains a hydroxyl group of a primary or secondary amino group as a functional group bonded directly or in a side chain.

A) in a first step completely or partly with a diisocyanate which forms a bridge group Q in an inert organic solvent, and in a second step reacting the product completely or partly with an aliphatic, cycloaliphatic, heterocycloaliphatic, aromatic or heteroaromatic ditertiary diphosphine, the phosphine groups of which are bonded with a carbon chain in the 1,2-, 1,3-, 1,4- or 1,5-position relative to one another and which contains a hydroxyl group or a primary or secondary amino group; or B) in a first step, reacting an aliphatic, cycloaliphatic, heterocycloaliphatic, aromatic or heteroaromatic ditertiary diphosphine, the phosphine groups of which are bonded to a carbon chain in the 1,2-, 1,3-, 1,4- or 1,5-position relative to one another and which contains a hydroxyl group or a primary or secondary amino group, completely or partly with a diisocyanate which forms a bridge group Q in an inert organic solvent and, in a second step, reacting the product completely or partly with a polymer having recurring structural elements of at least one monomer MM which contains a bonded hydroxyl group or a primary or secondary amino group as a functional group; and C) crosslinking any free isocyanate groups with a $C_2$–$C_{24}$diol or $C_2$–$C_{24}$diamine or reacting them with a $C_2$–$C_{12}$alcohol or $C_2$–$C_{12}$amine.

A polyalkylene glycol can also be used instead of a diol or diamine in reaction step C). If polyalkylene glycol which is etherified on one side is used, the alcohol or the amine can be replaced by this.

Examples of polyalkylene glycols are polyethylene glycol and polypropylene glycol. They preferably contain 2–1000 alkylene units.

The polyalkylene glycols which are etherified on one side are preferably the methyl, ethyl, propyl or butyl ether.

The bridge group Q, the 1,2-, 1,3-, 1,4- or 1,5- diphosphines and the polymers formed by the monomers MM are as defined and preferred above.

A preferred process for the preparation of crosslinked polymers is obtained if the polymers having recurring structural elements of at least one monomer MM which contains a bonded hydroxyl group or a primary or secondary amino group as functional group A) are reacted completely or partly, in a first step, with a diisocyanate which forms a bridge group Q in an inert organic solvent and, in a second step, the product is reacted completely or partly with an aliphatic, cycloaliphatic, heterocycloaliphatic, aromatic or heteroaromatic ditertiary diphosphine, the phosphine groups of which are bonded to a carbon chain in the 1,2-, 1,3-, 1,4- or 1,5- position relative to one another and which contains a hydroxyl group or a primary or secondary amino group, and the remaining diisocyanate groups are crosslinked with an aliphatic $C_2$–$C_{24}$diol or $C_2$–$C_{24}$diamine.

Another preferred process for the preparation of polymers is obtained if the polymers having recurring structural elements of at least one monomer MM which contains a bonded hydroxyl group or primary or secondary amino group as the functional group A) are reacted completely or partly, in a first step, with a diisocyanate which forms a bridge group Q in an inert organic solvent and, in a second step, the product is reacted completely or partly with an aliphatic, cycloaliphatic, heterocycloaliphatic, aromatic or heteroaromatic ditertiary diphosphine, the phosphine groups of which are bonded to a carbon chain in the 1,2-, 1,3-, 1,4- or 1,5-position and which contains a hydroxyl group or a primary or secondary amino group, and the remaining diisocyanate groups are reacted with an aliphatic $C_2$–$C_{12}$alcohol or $C_2$–$C_{12}$amine.

The polymer can subsequently also be modified in its properties in a controlled manner in this way.

If crosslinked polymers are prepared, preferably 0.01 to 10 mol per cent of the total isocyanate groups present are crosslinked.

The process is preferably carried out in a polar or non-polar aprotic solvent, and the solvent is particularly preferably a halogenated hydrocarbon, an ester, a ketone, an acid amide, ether, dimethyl sulfoxide or an aromatic compound.

The reaction of the hydroxyl group or the primary or secondary amino group is carried out by known processes preferably in a temperature range from 10° C. to 100° C.

Subsequent introduction, for example, of a hydroxy group into highly crosslinked polystyrene can be carried out by known processes. The polystyrene is first chloromethylated as described in J. Mol. Catal. 51 (1989), 13–27 and then hydrolysed by the method described by J. M. Frechet et al. in Polymer, 20 (1979) 675–680.

Subsequent modification can also be carried out in bulk for example using plasma processes. Chemical processes in solution or emulsion are also possible.

Insoluble polymers are ground and brought to the desired particle size by known processes beforehand.

The invention also relates to metal complexes of rhodium or iridium with polymeric 1,2-, 1,3-, 1,4- or 1,5 diphosphines of the formula IIIa or IIIb POL (YMeZ) (IIIa) POL (YMe)⁺A⁻ (IIIb), wherein POL is a polymer-bonded diphosphine according to the invention, Y is two monoolefin ligands or one diene ligand;

Z is —Cl, —Br, or —I;

A⁻ is the anion of an oxygen acid or complex acid and

13

Me is rhodium or iridium.

Metal complexes in which Y is 1,5-hexadiene, 1,5-cyclooctadiene or norbornadiene are preferred.

In metal complexes of the invention Z is preferably —Cl, —Br or I.

In the preferred metal complexes, $A^-$ is $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$ or $SbF_6^-$.

Preferred metal complexes are those in which the diphosphine ligand is a compound of the formula Ia or Ib.

The various radicals are as defined and preferred above.

The invention also relates to a process for the preparation of the metal complexes according to the invention, which comprises reacting the polymer-bonded diphosphines according to the invention with a metal compound of the formula $|Me(Y)Z|_2$ or $Me(Y)_2^+ A^-$, in which Me is rhodium or iridium and Y, Z and $A^-$ are as defined above.

The reaction is advantageously carried out under an inert gas atmosphere, for example argon, and expediently at temperatures from 0° to 40° C., preferably at room temperature, if the polymer-bonded diphosphines are soluble. A solvent or mixture of solvents is advantageously co-used, for example hydrocarbons (benzene, toluene, xylene), halogenated hydrocarbons (methylene chloride, chloroform, carbon tetrachloride, chlorobenzene), alkanols (methanol, ethanol, ethylene glycol monomethyl ether), and ethers (diethyl ether, dibutyl ether, tetrahydrofuran, ethylene glycol dimethyl ether), or mixtures thereof.

In the case of the polymer-bonded metal complexes according to the invention, a precalculated amount of this catalyst solution can be used directly for a hydrogenation reaction.

It is also possible to prepare the catalyst directly in situ in the hydrogenation solution. In the case of insoluble, soluble, partly or highly crosslinked polymer-bonded diphosphines, the metal compounds of the formula $|Me(Y)Z|_2$ or $Me(Y)_2^+ A^-$ are first dissolved in a solvent and this solution is added to the dissolved or foamed material. The reaction conditions described above can be used for this process. The polymer according to the invention can be either used directly or isolated by filtration, and purified by washing with the solvents mentioned above and dried in vacuum.

The polymeric metal complexes according to the invention are outstandingly suitable as catalysts for hydrogenation of unsaturatedorganic compounds having double or triple bonds, in particular as homogeneous, easily removable or heterogeneous catalysts for enantioselective hydrogenation of compounds having prochiral carbon and carbon/heteroatom double bonds, for example compounds which contain one of the groups C=C, C=N, C=O, C=C—N or C=C—O (cf. for example, K. E. Konig, The Applicability of Asymmetric Homogeneous Catalysis, in James D. Morrison (editor), Asymmetric Synthesis, Volume 5, Academic Press, 1985). Examples of such compounds are prochiral alkenes, imines and ketones. After the reaction, the catalysts according to the invention can be separated off almost completely from the reaction mixture in a simple manner, for example by decanting or filtration or, in the case of homogeneous catalysts, by precipitation, and then re-used several times. A significantly lower loss in activity is observed with these compared with known polymer-bonded catalysts. If desired, this loss can be compensated by addition of small amounts of fresh catalyst. Furthermore, comparable selectivities (optical yields) are achieved compared with homogeneous catalysts.

The invention therefore also relates to the use of the metal complexes according to the invention as heterogeneous or homogeneous catalysts for the hydrogenation of unsaturated organic compounds, preferably for asymmetric hydrogenation of prochiral compounds having carbon or carbon/heteroatom double bonds.

The metal complexes are preferably used for hydrogenation of asymmetric carbon double bonds, ketimines and ketones in prochiral organic compounds.

The invention also relates to a process for the hydrogenation of unsaturated organic compounds, preferably for asymmetric hydrogenation of prochiral organic compounds having carbon or carbon-heteroatom double bonds, which comprises hydrogenating the compounds at a temperature of −20° to 80° C. under a hydrogen pressure of $10^5$ to $2 \times 10^7$ Pa in the presence of catalytic amounts of one or more complexes according to the invention.

Preferred compounds have been mentioned above. Unsymmetric ketimines and ketones are known. N-arylketimines are described, for example, in EP-A-0 256 982. N-aliphatic ketimines are described, for example, in EP-A-0 301 457. Such imines can be prepared from the corresponding unsymmetric ketones, which are known and in some cases are commercially obtainable or can be prepared by known processes. Suitable substituted or unsubstituted alkenes are described in the abovementioned publication by K. E. König.

The process is preferably carried out at a temperature from −20° to 50° C., and preferably under a hydrogen pressure of $10^5$ to $10^7$ Pa.

The amount of catalyst is preferably chosen such that the molar ratio of the compound to be hydrogenated to the active catalyst constituent bonded to the polymer is 100 000 to 40.

A preferred process procedure comprises additionally co-using an ammonium- or alkali metal chloride, bromide or -iodide, especially if iridium catalysts according to the invention are used. The amount can be, for example, 0.1 to 100, preferably 1 to 50, and particularly preferably 2 to 20 equivalents, based on the active catalyst constituent fixed to the carrier. The addition of iodides is preferred. Ammonium is preferably tetraalkylammonium having 1 to 6 C atoms in the alkyl groups, and lithium, sodium or potassium is preferred as the alkali metal.

The hydrogenation can be carried out without or in the presence of solvents. Suitable solvents, which can be employed by themselves or as a mixture of solvents, are, for example: aliphatic and aromatic hydrocarbons (pentane, hexane, cyclohexane, methylcyclohexane, benzene, toluene, xylene), alcohols (methanol, propanol, butanol, ethylene glycol monomethyl ether), ethers (diethyl ether, diethylene glycol dimethyl ether, tetrahydrofuran, dioxane), halogenatedhydrocarbons (methylene chloride, chloroform, 1,1,2,2-tetrachloroethane, chlorobenzene), carboxylic acid esters and lactones (ethyl acetate, butyrolactone, valerolactone) and N-substituted acid amides and lactams (dimethylformamide, N-methylpyrrolidine). Mixtures of an aromatic hydrocarbon and alcohols, for example toluene/ethanol or benzene/methanol, are advantageous.

Optically pure compounds which are valuable intermediates for the preparation of biologically active ingredients, especially in the field of pharmaceuticals and agrochemicals, can be obtained with the hydrogenation process according to the invention. Thus, for example, from secondary amines, in particular N-carbalkoxymethylamines, it is possible to prepare 5-imidazolecarboxylic acid derivatives, which have a herbicidal action and can be used for weed control (EP-A-0 207 563). The optically pure α-aminocarboxylic acid esters are suitable for peptide syntheses.

The following examples illustrate the invention.
Abbreviations used:

TDI Tolylene 2,4-diisocyanate

HDI Hexamethylene 1,6-diisocyanate

PPM (2S,4S)-(-)-4-Diphenylphosphino-2-(diphenylphosphinomethyl)-pyrrolidine

DMF N,N-Dimethylformamide

PKHH: Polyphenoxy resin based on bisphenol A. Average molecular weight about 50 000 D. Supplier: Union Carbide.

HEMA: Poly(2-hydroxyethyl methacrylate). Supplier: Aldrich (No. 19,206-6).

XAD-2: Macroporous, highly crosslinked polystyrene beads, 20–50 mesh. Supplier: Rohm & Haas Co.

PS—$CH_2$—$NH_2$: Aminomethylated polystyrene beads crosslinked with 1% of divinylbenzene.
Amine content: 0.56 mmol/g. Supplier: Novabiochem AG, CH4448 Laufelfingen, Switzerland.

PS—PEG—OH: Polyethylene glycol 600 bonded to polystyrene-1% divinylbenzene. Supplier: Fluka (No. 81185).

All the following reactions of Examples A1 to A17 were carried out under an argon atmosphere using absolute solvents.

EXAMPLES A

Preparation of Immobilized Ligands

EXAMPLES A1–A9

Preparation Starting from Soluble, Non-Crosslinked Polymers which are Reacted with a Diisocyanate in a First Step Example A1

1.17 ml (8.16 mmol) of TDI (tolylene 2,4-diisocyanate) are added dropwise to a solution of 145 mg (0.51 mmol of OH-groups) of polyphenoxy resin based on bisphenol A-diglycidyl ether (PKHH-polymer, average molecular weight about 50 000 D. Supplier: Union Carbide) in 7 ml of $CH_2Cl_2$. After addition of 8 μl of triethylamine as catalyst, the reaction solution is stirred at 45°–50° C. for 3.5 hours. After cooling the solution to room temperature, the excess TDI is removed by repeating the following operation 5 times: precipitation of the polymers with 50 ml of hexane, decanting of the supernatant solution, redissolving of the polymer with 7 ml of $CH_2Cl_2$. 231 mg (0.51 mmol) of PPM (2S,4S)-(-)-4-diphenylphosphino-2-(diphenylphosphinomethyl)-pyrrolidine are then added to the polymer in 10 ml of $CH_2Cl_2$ and the mixture is stirred for 20 hours. In order to react isocyanate groups which have not yet reacted, 5 ml of ethanol and 10 μl of triethylamine (catalyst) are then added dropwise and the reaction mixture is stirred under reflux for 2.5 hours. The ligand fixed to the polymer is then washed by repeating the following operation 6 times: precipitation with 100 ml of hexane, decanting of the supernatant solution, dissolving/swelling of the residue with 15 ml of $CH_2Cl_2$. After the last washing operation, the residue is dried under a high vacuum. A white powder which is substantially soluble in $CH_2Cl_2$ is obtained.

Analysis: Microanalysis: Phosphorus content=6.25%. This corresponds to 1.01 mmol of diphosphine ligand/g.

Example A2

2.84 ml (19.8 mmol) of TDI are added dropwise to a solution of 350 mg (1.23 mmol of OH groups) of PKHH polymer in 10 ml of $CH_2Cl_2$. After addition of 20 μl of triethylamine as a catalyst, the reaction solution is stirred at 45°–50° C. for 3.5 hours. After cooling the solution to room temperature, the excess TDI is removed by repeating the following operating 5 times: precipitation of the polymer with 50 ml of hexane, decanting of the supernatant solution, redissolving of the polymer with 10 ml of $CH_2Cl_2$. After the last decanting, the polymer is dissolved in 10 ml of $CH_2Cl_2$ and, after addition of 140 mg (0.31 mmol) of PPM the reaction mixture is stirred at room temperature for 20 hours. The remaining isocyanate groups are then reacted with ethanol (5 ml) in the presence of 20 μl of triethylamine by stirring at 50° C. (4 hours). The ligand fixed to the polymer is then washed by repeating the following operation 5 times: precipitation with 50 ml of hexane/diethyl ether (3/2), decanting of the supernatant solution, dissolving/swelling of the residue with 10 ml of $CH_2Cl_2$. After the last washing operation, the residue is finally dried under a high vacuum. A white powder which is substantially soluble in $CH_2Cl_2$ is obtained.

Analysis: Microanalysis: phosphorus content=2.35 %. This corresponds to 0.379 mmol of diphosphine ligand/g.

Example A3

3.04 ml (21.1 mmol) of TDI are added dropwise to a solution of 375 mg (1.32 mmol of OH groups) of PKHH polymer in 10 ml of $CH_2Cl_2$. After addition of 20 μl of triethylamine as a catalyst, the reaction solution is stirred at 45°–50° C. for 3.5 hours. After cooling the solution to room temperature, the excess TDI is removed by repeating the following operation 5 times: precipitation of the polymer with 50 ml of hexane, decanting of the supernatant solution, redissolving of the polymer with 10 ml of $CH_2Cl_2$. After the last decanting, the polymer is dissolved in 10 ml of $CH_2Cl_2$ and, after addition of 150 mg (0.33 mmol) of PPM the reaction mixture is stirred at room temperature for 20 hours. The remaining isocyanate groups are then reacted with diethylene glycol monomethyl ether (5 ml) in the presence of 20 μl of triethylamine by stirring at 50° C. (20 hours). The ligand fixed to the polymer is then washed by repeating the following operation 5 times: precipitation with 100 ml of hexane, decanting of the supernatant solution, dissolving/swelling of the residue with 15 ml of $CH_2Cl_2$. After the last washing operation, the residue is finally dried under a high vacuum. A white powder which swells to a high degree in $CH_2Cl_2$ is obtained.

Analysis: Microanalysis: phosphorus content=1.53 %. This corresponds to 0.247 mmol of diphosphine ligand/g.

Example A4

2.06 ml (14.3 mmol) of TDI are added dropwise to a solution of 117 mg (0.9 mmol of OH groups) of poly(2-hydroxyethyl methacrylate) (HEMA polymer, Supplier: Aldrich) in 5 ml of DMF (N,N-dimethylformamide). After addition of 15 μl of triethylamine as a catalyst, the reaction solution is stirred at 65° C. for 30 minutes. After cooling the solution to room temperature, the excess TDI is removed by repeating the following operation 4 times: precipitation of the polymer with 25 ml of diethyl ether/hexane (3/2), decanting of the supernatant solution, redissolving of the polymer with 5 ml of DMF. After the last decanting, the polymer is swelled in 5 ml of DMF and, after addition of 102 mg (0.23 mmol) of PPM, the reaction mixture is stirred at room temperature for 20 hours. The remaining isocyanate groups are then reacted with ethanol (5 ml) in the presence of 20 μl of triethylamine by stirring at 60° C. (22 hours). The ligand fixed to the polymer is then washed by repeating the following operation 5 times: precipitation with 50 ml of diethyl ether, decanting of the supernatant solution, dissolving/swelling of the residue with 10 ml of ethanol. After the last washing operation, the residue is finally dried under a high vacuum. A white powder.

Analysis: Microanalysis: phosphorus content=2.69 %. This corresponds to 0.434 mmol of diphosphine ligand/g.

Example A5

2.8 ml (19.4 mmol) of TDI are added dropwise to a solution of 344 mg (1.21 mmol of OH groups) of PKHH polymer in 16 ml of $CH_2Cl_2$. After addition of 20 µl of triethylamine as a catalyst, the reaction solution is stirred at 45°–50° C. for 4.5 hours. After cooling the solution to room temperature, the excess TDI is removed by repeating the following operation 5 times: precipitation of the polymer with 50 ml of hexane, decanting of the supernatant solution, redissolving of the polymer with 10 ml of $CH_2Cl_2$. After the last decanting, the polymer is dissolved in 16 ml of $CH_2Cl_2$ and, after addition of 137 mg (0.3 mmol) of PPM the reaction mixture is stirred at room temperature for 20 hours. The polymer is crosslinked slightly by addition of 0.5 ml of polyethylene glycol (molecular weight 190–210 D) and 5 µl of triethylamine as a catalyst and stirring at 50° C. (1 hour). The remaining isocyanate groups are then reacted with ethanol (8 ml) in the presence of a further 5 µl of triethylamine by stirring at 50° C. (16 hours). The ligand fixed to the polymer is then washed by repeating the following operation 5 times: precipitation with 50 ml of hexane, decanting of the supernatant solution, swelling of the residue with 10 ml of $CH_2Cl_2$. After the last washing operation, the residue is finally dried under a high vacuum. A white powder which swells in $CH_2Cl_2$ provides a gel.

Analysis: Microanalysis: phosphorus content=1.69 %. This corresponds to 0.273 mmol of diphosphine ligand/g.

Example A6

1.25 ml (8.8 mmol) of TDI are added dropwise to a solution of 622 mg (2.2 mmol of OH groups) of PKHH polymer in 13 ml of $CHCl_3$. After addition of 5 µl of triethylamine as a catalyst, the reaction solution is stirred at 50° C. for 100 minutes. After cooling the solution to room temperature, the excess TDI is removed by repeating the following operation twice: precipitation of the polymer with0 50 ml of hexane, decanting of the supernatant solution, redissolving of the polymer with 15 ml of $CHCl_3$. After the last decanting, the polymer is dissolved in 20 ml of $CHCl_3$. 250 mg (0.55 mmol) of PPM are added and the reaction mixture is stirred at room temperature for 20 hours. Unreacted isocyanate groups are then reacted with ethanol (10 ml) in the presence of 5 µl of triethylamine by stirring at 45° C. (3 hours). The ligand fixed to the polymer is then washed by repeating the following operation twice: precipitation with 50 ml of diethyl ether, decanting of the supernatant solution, dissolving/swelling of the residue with 15 ml of $CHCl_3$. After the last washing operation, the residue is finally dried under a high vacuum. A white powder which is substantially soluble in $CH_2Cl_2$ is obtained.

Analysis: Microanalysis: phosphorus content=2.55 %. This corresponds to 0.411 mmol of diphosphine ligand/g.

Example A7

1.06 ml (7.4 mmol) of TDI are added dropwise to a solution of 525 mg (1.8 mmol of OH groups) of PKHH polymer in 12 ml of $CHCl_3$. After addition of 5 µl of triethylamine as a catalyst, the reaction solution is stirred at 50° C. for 60 minutes. After cooling the solution to room temperature, the excess TDI is removed by repeating the following operation twice: precipitation of the polymer with 50 ml of hexane, decanting of the supernatant solution, redissolving of the polymer with 15 ml of $CHCl_3$. After the last decanting, the polymer is dissolved in 15 ml of $CHCl_3$. 203 mg (0.46 mmol) of (3R,4R)-3,4-(bisdiphenylphosphine) pyrrolidine are then added and the reaction mixture is stirred at room temperature for 6 hours. Unreacted isocyanate groups are then reacted with ethanol (5 ml) in the presence of 5 µl of triethylamine by stirring at 45° C., (1 hour). The ligand fixed to the polymer is then washed by repeating the following operation twice: precipitation with 50 ml of diethylether, decanting of the supernatant solution, dissolving/swelling of the residue with 10 ml of $CHCl_3$. After the last washing operation, the residue is finally dried under a high vacuum. A white powder which is substantially soluble in $CH_2Cl_2$ is obtained.

Analysis: Microanalysis: phosphorus content=2.85 %. This corresponds to 0.46 mmol of diphosphine ligand/g.

Example A8

1.08 ml (7.5 mmol) of TDI are added dropwise to a solution of 530 mg (1.9 mmol of OH groups) of PKHH polymer in 12 ml of $CHCl_3$. After addition of 5 µl of triethylamine as a catalyst, the reaction solution is stirred at 50° C. for 60 minutes. After cooling the solution to room temperature, the excess TDI is removed by repeating the following operation twice: precipitation of the polymer with 50 ml of hexane, decanting of the supernatant solution, redissolving of the polymer with 15 ml of $CHCl_3$. After the last decanting, the polymer is dissolved in 20 ml of $CHCl_3$. 253 mg (0.47 mmol) of (4S,5S)-1-methyl-1'-(4-aminobutyl)-4,5-bis|(diphenylphosphino)methyl|-1,3-dioxolane are added and the reaction mixture is stirred at room temperature for 20 hours. Unreacted isocyanate groups are then reacted with ethanol (5 ml) in the presence of 5 µl of triethylamine by stirring at 45° C. (3 hours). The ligand fixed to the polymer is then washed by repeating the following operation twice: precipitation with 100 ml of diethylether, decanting of the supernatant solution, dissolving/swelling of the residue with 15 ml of $CHCl_3$. After the last washing operation, the residue is finally dried under a high vacuum. A white powder which is substantially soluble in $CH_2Cl_2$ is obtained.

Analysis: Microanalysis: phosphorus content=2.73 %. This corresponds to 0.404 mmol of diphosphine ligand/g.

Example A9

0.085 ml (0.59 mmol) of TDI are added dropwise to a solution of 334 mg (1.17 mmol of OH groups) of PKHH polymer in 10 ml of $CH_2Cl_2$. After addition of 10 µl of triethylamine as a catalyst, the reaction solution is stirred at 45°–50° C. for 3.5 hours. A gel is formed from the previously soluble polymer by this operation. After cooling the solution to room temperature, the unreacted TDI is removed by repeating the following operation 5 times: precipitation of the polymer with 50 ml of hexane, decanting of the supernatant solution, re-swelling of the polymer with 20 ml of $CH_2Cl_2$. After the last decanting, the polymer is suspended in 20 ml of $CH_2Cl_2$. 133 mg (0.29 mmol) of PPM are then added and the reaction mixture is stirred at room temperature for 20 hours. Unreacted isocyanate groups are then reacted by addition of ethanol (5 ml) in the presence of 20 µl of triethylamine and stirring at 50° C. (20 hours). The ligand fixed to the polymer is then washed by repeating the following operation 5 times: precipitation with 50 ml of hexane, decanting of the supernatant solution, dissolving/swelling of the residue with 20 ml of $CH_2Cl_2$. After the last washing operation, the residue is finally dried under a high vacuum. A white powder which forms a gel in $CH_2Cl_2$ is obtained.

Analysis: Microanalysis: phosphorus content=2.80 %. This corresponds to 0.45 mmol of diphosphine ligand/g.

EXAMPLES A10–A13

Preparation Starting from Crosslinked Polymers which are Reacted with a Diisocyanate in a First Step

Example A10

Highly crosslinked, macroporous polystyrene (XAD-2, beads, 20–50 mesh. Supplier: Rohm & Haas Co.) was chloromethylated by the method of G. Challa et al. (J. Mol. Catal., 51 (1989) 13–27) and then hydrolysed by the method of J. M. J Frechet et al. (Polymer, 20 (1979) 675–680) (O content=1.49 mmol/g). 0.72 ml (5 mmol) of TDI is added dropwise to a suspension of 600 mg (0.89 mmol of OH groups) of this hydroxymethylated XAD-2 in 10 ml $CH_2Cl_2$. After addition of 5 µl of triethylamine as a catalyst, the reaction solution is stirred at 45°–50° C. for 4 hours. After cooling the solution to room temperature, the excess TDI is removed by washing 5 times with $CH_2Cl_2$. The polymer is then suspended in 10 ml of $CH_2Cl_2$ and, after addition of 401 mg (0.88 mmol) of PPM, the reaction mixture is stirred at room temperature for 20 hours. The remaining isocyanate groups are then reacted with ethanol (5 ml) in the presence of 5 µl of triethylamine by stirring at 40° C. (9 hours). The ligand fixed to the polymer is then washed 6 times with 10 ml of $CH_2Cl_2$ each time and finally dried under a high vacuum. A white insoluble powder is obtained.

Analysis: Microanalysis: phosphorus content=1.34 %. This corresponds to 0.216 mmol of diphosphine ligand/g.

Example A11

1 g of PS—$CH_2$—$NH_2$ polymer (PS—$CH_2$—$NH_2$: aminomethylated polystyrene beads crosslinked with 1% of divinylbenzene, amine content: 0.56 mmol/g; Supplier: Novabiochem AG, CH-4448 Laufelfingen, Switzerland) swollen in 40 ml of $CH_2Cl_2$ is stirred in the presence of 1.3 ml (9.1 mmol) of TDI at room temperature for 1 hour. The excess TDI is then removed by washing 4 times with 40 ml of $CH_2Cl_2$ each time, the support is taken up again in 30 ml of $CH_2Cl_2$ and, after addition of 259 mg (0.57 mmol) of PPM, the mixture is stirred at room temperature for 4 hours. To react the remaining isocyanate groups, 10 ml of ethanol and 20 µl of triethylamine are added and the mixture is stirred at room temperature for 40 hours. The ligand fixed to the polymer is then washed 5 times with 40 ml of $CH_2Cl_2$ each time and finally dried under a high vacuum. White beads are obtained, the swelling properties of which have remained unchanged compared with the support used.

Analysis: Microanalysis: phosphorus content=1.17 %. This corresponds to 0.189 mmol of diphosphine ligand/g.

Example A12

980 mg of PS—$CH_2$—$NH_2$ polymer swollen in 40 ml of $CH_2Cl_2$ are stirred in the presence of 1.77 ml (11 mmol) of HDI (HDI: hexamethylene 1,6-diisocyanate) at 40° C. for 1 hour. The excess HDI is then removed by washing 5 times with 20 ml of $CH_2Cl_2$ each time, the support is taken up again in 20 ml of $CH_2Cl_2$ and, after addition of 250 mg (0.55 mmol) of PPM, the mixture is stirred at room temperature for 18 hours. To react the remaining isocyanate groups, 10 ml of ethanol and 30 µl of triethylamine are added and the mixture is stirred at 40° C. for 16 hours. The ligand fixed to the polymer is then washed 6 times with 20 ml of $CH_2Cl_2$ each time and finally dried under a high vacuum. White beads, the swelling properties of which have remained unchanged with respect to the support employed are obtained.

Analysis: Microanalysis: phosphorus content=1.17 %. This corresponds to 0.189 mmol of diphosphine ligand/g.

Example A13

Commercially obtainable chloromethylated polystyrene crosslinked with 1% of divinylbenzene (Cl content=0.7 mmol/g; from Novabiochem AG) is hydrolysed by the method of J. M. J Frechet et al. (Polymer, 20 (1979) 675–680). 3.2 g of this material, which is swollen beforehand in 38 ml of methylene chloride, are stirred in the presence of 6 ml of TDI and 50 µl of triethylamine as a catalyst at 50° C. overnight. After cooling the solution to room temperature, the excess TDI is removed by washing 4 times with 70 ml of $CH_2Cl_2$ each time. The polymer is then suspended in 70 ml of $CH_2Cl_2$ and, after addition of 300 mg (0.66 mmol) of PPM, the reaction mixture is stirred at room temperature for 15 hours. The remaining isocyanate groups are then reacted with ethanol (5 ml) in the presence of 40 µl of triethylamine by stirring at 50° C. (7 hours). The ligand fixed to the polymer is then washed 5 times with 70 ml of $CH_2Cl_2$ each time and finally dried under a high vacuum. White beads, the swelling properties of which have remained practically unchanged compared with the non-modified polymer, are obtained.

Analysis: Microanalysis: phosphorus content =0.93 %. This corresponds to 0.150 mmol of diphosphine ligand/g.

EXAMPLES A14–16

Preparation Starting from Soluble, Non-crosslinked Polymers, the Diphosphine Ligand being Reacted with a Diisocyanate in a First Reaction Step

Example A14

Reaction of the Diphosphine Ligand with a Diisocyanate which forms a Bridge Group A solution of 180 mg (0.4 mmol) of PPM |(2S,4S)-(-)-4-diphenylphosphino-2-(diphenylphosphinomethyl)pyrrolidine| in 3 ml of $CH_2Cl_2$ is added dropwise to a solution of 0.58 ml (4 mmol) of TDI in 4 ml of $CH_2Cl_2$ at −50° C. After stirring for 1 hour, the cooling is removed and the reaction solution is evaporated in vacuo at room temperature. After addition of 25 ml of hexane and vigorous stirring, the oily residue solidifies. This is then freed from excess TDI by washing 5 times with 30 ml of hexane each time and is finally dried under a high vacuum at room temperature. The diphosphine functionalized in this way is further used immediately for Examples A13 and A14.

Example A15

A solution of 100 mg (about 0.16 mmol) of the ligand prepared in Example A13 in 3 ml of $CH_2Cl_2$ is added dropwise to a solution of 182 mg (0.65 mmol of OH groups) of PKHH polymer. After addition of 10 µl of triethylamine as a catalyst, the solution is stirred under reflux for 48 hours. The ligand fixed to the polymer is then washed by repeating the following operation 5 times: precipitation with 30 ml of hexane/diethyl ether (2/1), decanting of the supernatant solution, dissolving/swelling of the residue with 5 ml of $CH_2Cl_2$. After the last washing operation, the residue is finally dried under a high vacuum. A white powder which swells in $CH_2Cl_2$ is obtained.

Analysis: Microanalysis: phosphorus content=2.9 %. This corresponds to 0.47 mmol of diphosphine ligand/g.

Example A16

A solution of 170 mg (about 0.27 mmol) of the ligand prepared in Example A13 in 3 ml of DMF is added dropwise to a solution of 100 mg (0.77 mmol of OH groups) of HEMA polymer in 2 ml of DMF. After addition of 10 μl of triethylamine as a catalyst, the solution is stirred at 56° C. for 16 hours. The ligand fixed to the polymer is then washed by repeating the following operation 6 times: precipitation with 50 ml of hexane/diethyl ether (4/1), decanting of the supernatant solution, dissolving/suspending of the residue in 3 ml of DMF. After the last washing operation, the residue is finally dried under a high vacuum. A white powder which swells in DMF is obtained.

Analysis: Microanalysis: phosphorus content=3.1 %. This corresponds to 0.5 mmol of diphosphine ligand/g.

EXAMPLES A17, A18

Preparation Starting from Crosslinked Polymers, the Diphosphine Ligand being Reacted with a Diisocyanate in a First Reaction Step

Example A17

Immobilization on PS—PEG—OH (polyethylene glycol 600 bonded to polystyrene- % divinylbenzene. Supplier: Fluka (No. 81185))

A solution of 130 mg (about 0.2 mmol) of the ligand prepared in Example A13 in 3 ml of $CH_2Cl_2$ is added dropwise to a suspension of 2 g (0.7 mmol of OH groups) of polymer in 12 ml of $CH_2Cl_2$. After addition of 10 μl of triethylamine as a catalyst, the solution is stirred under reflux for 20 hours. The ligand fixed to the polymer is then washed 4 times with 20 ml of $CH_2Cl_2$ each time and finally dried under a high vacuum. A pale beige powder is obtained.

Analysis: Microanalysis: phosphorus content=0.4 %. This corresponds to 0.065 mmol of diphosphine ligand/g.

Example A18

A solution of 255 mg (0.56 mmol) of PPM ligand |(2S, 4S)-(-)-4-diphenylphosphino-2-(diphenylphosphinomethyl)pyrrolidine| in 10 ml of $CH_2Cl_2$ is added dropwise to a solution of 0.081 ml (0.56 mmol) of TDI in 10 ml of $CH_2Cl_2$ at −70° C. in the course of 3 hours. The solution is allowed to warm to room temperature and is added to 1 g of PS—$CH_2$—$NH_2$ polymer in 20 ml of $CH_2Cl_2$, and the mixture is stirred. After 16 hours, to react still free amino groups of the polymer, 0.13 ml (1.13 mmol) of butyl isocyanate is added and the mixture is stirred for a further 90 minutes. The polymer-bonded ligand is then filtered off and washed 3 times with 40 ml of $CH_2Cl_2$ each time. To react any unreacted isocyanate groups, the mixture is then stirred in 40 ml of ethanol/$CH_2Cl_2$ (1/1) and 30 μl of triethylamine for 20 hours. Finally, it is washed again with 4 portions of 40 ml of $CH_2Cl_2$ and the polymer is dried under a high vacuum. White beads, the swelling properties of which have remained unchanged compared with the support employed, are obtained.

Analysis: Microanalysis: phosphorus content =1.3 %. This corresponds to 0.21 mmol of diphosphine ligand/g.

EXAMPLES B1–B22

Hydrogenations a) General Procedure

Enantioselective catalytic hydrogenations are carried out with the polymer-bonded ligands 1–16. For this, these ligands are converted "in situ" into corresponding Rh catalysts. Methyl acetamidocinnamate is used as the hydrogenation substrate. All operations apart from the hydrogenation itself are carried out under argon, and degassed solvents are used. The courses of the reactions and the conversions are monitored by means of gas chromatography (GC): (Column: SE 54, Length: 15 m, carrier gas: He). The enantioselectivities are likewise determined by means of GC (Column: Chirasil-L-val, length 50 m, carrier gas: He).

b) Standard Procedure for the Hydrogenation

15 μmol of ligand are stirred in 5 ml of tetrahydrofuran (THF) or a mixture of THF and methanol (MeOH) for 15 minutes. (Note: Polymers which are soluble or swellable in THF or in MeOH dissolve or swell in this period of time.) A solution of 12.5 μmol of $|Rh(cyclooctadiene)_2|BF_4$ in 1 ml of MeOH is then added and stirring is continued for 15 minutes. (Note: During this operation, the swellable and the macroporous supports become yellow-orange in colour and the solution becomes colourless.) To the rhodium-diphospine complex prepared "in situ" in this manner, a solution of 2.5 mmol of methyl acetamidocinnamate is added as the substrate (substrate/catalyst=as a rule 200) in 16 ml of MeOH or MeOH/THF (cf. table). The mixture is then evacuated and $H_2$ passed in 3 times, and finally hydrogenation is carried out under a normal pressure of $H_2$, while stirring intensively with a magnetic stirrer.

Example B23

All the operations apart from the hydrogenation are carried out under an inert gas (argon). The ee determination is carried out by converting the sample of phenylalanine into phenylalanine methyl ester with $|Me_3O|BF_4$ and determining the ee by means of GC. Column: Chirasil-L-val, length 50 m, carrier gas He.

4.1 mg (0.01 mmol)of $|Rh(COD)_2|BF_4$, dissolved in 3 ml of MeOH, are added to a suspension of 86 mg (0.013 mmol) of the ligand from Example A13 in 3 ml of THF and the mixture is stirred. During this operation, the solution decolourizes and the immobilized ligand becomes orange in colour. 718 mg (3.5 mmol) of acetamidocinnamic acid dissolved in 8 ml of MeOH and 8 ml of THF are then added. The mixture is then evacuated and $H_2$ passed in 3 times and hydrogenation is finally carried out under a $H_2$ pressure of 1 bar, while stirring intensively (with a magnetic stirrer). After 3 hours, the hydrogenation is switched off. The conversion is complete and the ee is 97.7%.

The hydrogenation results are summarized in Table 1, the enantiomer excess is stated as "ee", and deviating process parameters are stated in the comments column.

TABLE 1

| No. | Ligand from example | Ratio Substrate/ catalyst | MeOH/ THF | Conversion % | Time minutes | ee % | Comments |
|---|---|---|---|---|---|---|---|
| B1 | A1 | 200 | 3.5/1 | 100 | 19 | 93.5 | |
| B2 | A1 | 200 | 1/21 | 100 | 39 | 80.5 | |
| B3 | A2 | 200 | 3.5/1 | 100 | 12 | 95 | 1) |
| B4 | A2 | 200 | 1/21 | 100 | 30 | 92 | |
| B5 | A3 | 200 | 3.5/1 | 100 | 20 | 93 | 1) |
| B6 | A4 | 200 | 3.5/1 | 100 | 15 | 90 | |
| B7 | A5 | 200 | 3.5/1 | 100 | 35 | 93 | |
| B8 | A5 | 200 | 1/21 | 100 | 32 | 83 | |
| B9 | A6 | 200 | 3.5/1 | 100 | 15 | 95.5 | |
| B10 | A6 | 200 | 1/21 | 100 | 26 | 94 | |
| B11 | A7 | 1000 | 3.5/1 | 100 | 37 | 89.2 | $H_2$ pressure of 55 bar steel autoclave |

TABLE 1-continued

| No. | Ligand from example | Ratio Substrate/ catalyst | MeOH/ THF | Conversion % | Time minutes | ee % | Comments |
|---|---|---|---|---|---|---|---|
| B12 | A7 | 1000 | 1.5/13 | 100 | 30 | 91.1 | $H_2$ pressure of 55 bar steel autoclave |
| B13 | A8 | 200 | 1/21 | 99 | 16 | 74 | |
| B14 | A9 | 200 | 3.5/1 | 100 | 15 | 95 | |
| B15 | A10 | 200 | 3.5/1 | 95 | 240 | 87 | |
| B16 | A11 | 200 | 1/1 | 80 | 105 | 91 | |
| B17 | A12 | 200 | 1/1 | 99 | 60 | 94.5 | |
| B18 | A15 | 200 | 3.5/1 | 100 | 29 | 94.8 | |
| B19 | A16 | 200 | 3.5/1 | 100 | 16 | 94.7 | [1] |
| B20 | A16 | 200 | 1/0 | 100 | 66 | 90.6 | [1] |
| B21 | A17 | 200 | 3.5/1 | 97 | 60 | 90 | |
| B22 | A18 | 200 | 1/1 | 50 | 125 | 90 | |
| B23 | A13 | 350 | 1/1 | 100 | 180 | 97.7 | |

[1] Examples which were separated by ultrafiltration, described as Examples C1–C4 below.

The catalysts which are fixed to swellable or macroporous (insoluble) supports (Examples A10–A13 and A16–A17) can be separated off by simple filtration or allowing to settle, or centrifugation and decanting. The resulting solutions are in each case colourless.

The catalysts fixed to soluble supports can be separated off by two different routes:

1) By precipitation after addition of a solvent (for example hexane) in which they are insoluble, and subsequent filtration.

2) By ultrafiltration.

C) Separation examples by ultrafiltration. Examples C1–C4

The reaction mixture is introduced into a filtration apparatus and forced through an ultrafiltration membrane, for example a polysulfone membrane of the Omega 3K type from Filtron or the UFM410 membrane from Amafilter, under a pressure of 5–10 bar. Colourless solutions are obtained. The results are shown in Table 2. The rhodium determination was carried out by means of ion-selective mass spectrometry.

TABLE 2

| No. | Hydrogenation experiment No. | Membrane | Loss of rhodium |
|---|---|---|---|
| C1 | B3 | UFM410 | 1.6% |
| C2 | B5 | UFM410 | 2% |
| C3 | B20 | Omega 3k | 5% |
| C4 | B21 | Omega 3k | 1.2% |

D) Re-use of the catalysts from Example B23

The colourless reaction solution from Example B23 is drawn off with a syringe after being rendered inert with argon. A solution of 718 mg (3.5 mmol) of acetamidocinnamic acid dissolved in 11 ml of MeOH and 11 ml of tetrahydrofuran is added to the catalyst which remains and hydrogenation is then carried out again as above. After 3 hours, the conversion is complete and an enantiomer excess ee of 96.9 % is obtained.

E) Imine hydrogenations with an Ir catalyst

Example E1

Preparation of N-(2'-methyl-6'-ethyl-phen-1'-yl)-N-(1-methoxymethyl)-ethylamine with immobilized ligand A13

All the manipulations are carried out under an inert gas, with the exception of the hydrogenation.

79 mg (0.0118 mmol) of ligand from Example A13 are stirred all at once into 2 ml of THF in the course of 5 minutes. A solution of 3.2 mg |Ir(COD)Cl|$_2$ (0.0098 mmol Ir) in 2 ml of THF is then added and the mixture is stirred slowly, the yellow solution decolourizing. 4.8 mg of tetrabutylammonium iodide and 2 g (9.8 mmol) of N-(2'-methyl-6'-ethyl-phen-1'-yl)-N-(1-methoxymethyl)-ethylimine are introduced into a second flask and the solution is placed under an inert gas and added to the catalyst. The reaction mixture is then forced into a 50 ml steel autoclave with a steel capillary under a countercurrent of inert gas and subsequently hydrogenated under a hydrogen pressure of 80 bar at 250 C. After 72 hours, the hydrogen is let down and the catalyst is filtered off. According to determination by gas chromatography, the conversion is 80%. The optical yield is determined by means of HPLC (Column: Chiracel OD) using a sample purified by flash chromatography (silica gel Merck 60, mobile phase=hexane/ ethyl acetate). The ee is 59.9% (R).

What is claimed is:

1. A polymer having recurring structural elements of at least one monomer MM which contains a hydroxyl group or a primary or secondary amine group as a functional group bonded directly or in a side chain, wherein the functional group is bonded via a bridge group Q formed by a diisocyanate to the hydroxyl group or primary or secondary amino group of an aliphatic, cycloaliphatic, heterocycloaliphatic, aromatic or heteroaromatic ditertiary diphosphine, the phosphine groups of which are bonded to a carbon chain in the 1,2-, 1,3-, 1,4- or 1,5-position relative to one another; wherein the hydroxyl-, or primary or secondary aminofunctional monomer participates from 5 to 100 mol per cent in the build-up of the polymer and wherein the molecular weight of the polymer is 2,000 to 5,000,000 Dalton.

2. A polymer according to claim 1, wherein Q is a linear or branched aliphatic $C_2$–$C_{20}$alkyl which is unsubstituted or mono- or polysubstituted by $C_1$–$C_6$alkyl or $C_1$–$C_6$alkoxy, $C_3$–$C_8$cycloalkyl or heterocycloalkyl which is unsubstituted or mono- or polysubstituted by $C_1$–$C_6$alkyl or $C_1$–$C_6$alkoxy, linear or branched aliphatic $C_1$–$C_{20}$alkyl which is interrupted by unsubstituted or $C_1$–$C_6$alkyl- or $C_1$–$C_6$alkoxy-substituted $C_3$–$C_8$cycloalkyl or heterocycloalkyl and is unsubstituted or substituted by $C_1$–$C_6$alkyl or $C_1$–$C_6$alkoxy, phenyl, naphthyl, biphenyl or $C_3$–$C_{10}$heteroaryl which is unsubstituted or mono- or polysubstituted by $C_1$–$C_6$alkyl or $C_1$–$C_6$alkoxy, or linear or branched aliphatic $C_2$–$C_{20}$alkyl which is interrupted by phenyl, naphthyl or $C_3$–$C_{10}$heteroaryl and is unsubstituted or substituted by $C_1$–$C_6$alkyl or $C_1$–$C_6$alkoxy.

3. A polymer according to claim 1, wherein the diisocyanate forming the bridge group Q is chosen from the group consisting of 1,6-bis|isocyanato|hexane, 5-isocyanato-3-(isocyanatomethyl)-1,1,3-trimethylcyclohexane 1,3-bis|5-isocyanato-1,3,3-trimethylphenyl|-2,4-dioxo- 1,3-diazetidine, 3,6-bis|9-isocyanatononyl|4,5-di(1 -heptenyl) cyclohexene, bis|4-isocyanatocyclohexyl|methane, trans-1, 4-bis|isocyanato|cyclohexane, 1,3-bis|isocyanatomethyl| benzene, 1,3-bis|1-isocyanato-1-methylethyl|benzene, 1,4-bis|2-isocyanatoethyl|cyclohexane, 1,3-bis |isocyanatomethyl|cyclohexane, 1,4-bis|1-isocyanato-1- methylethyl|benzene, bis|isocyanato|isododecylbenzene.1, 4-bis|isocyanato|benzene, 2,4-bis|isocyanato|toluene, 2,6-bis|isocyanato|toluene, 2,4-/2,6-bis|isocyanato|toluene, 2-ethyl-1 ,2, 3-tris|3-isocyanato-4-methylanilinocarbonyloxy|propane, N,N'-bis|3-isocyanato-4-methylphenyl|urea, 1,4-bis|3-isocyanato-4-methylphenyl|-2,4-dioxo-1,3-diazetidine, 1,3,5-tris-|3-isocyanato-4-methylphenyl|-2,4,6-trioxohexahydro-1,3,5-triazine, 1,3-bis|3-isocyanato-4-methylphenyl|-2,4,5-trioxoimidazolidine, bis|2-isocyanatophenyl|methane, (2-isocyanatophenyl)(4-isocyanatophenyl)methane, bis|4-isocyanatophenyl|methane, 2,4-bis|4-isocyanatobenzyl|-1-isocyanatobenzene, |4-isocyanato-3-(4-isocyanatobenzyl)-phenyl||2-isocyanato-5-(4-isocyanatobenzyl)phenyl|methane, tris|4-isocyanatophenyl|methane, 1,5-bis|isocyanato|naphthalene and 4,4'-bis|isocyanato|-3,3'-dimethylbiphenyl.

4. A polymer according to claim 3, wherein the diisocyanate which forms the bridge group Q is chosen from the group consisting of 1,6-bis|isocyanato|hexane, 5-isocyanato-3-(isocyanatomethyl)-1,1,3-trimethylcyclohexane, 2,4-bis|isocyanato|toluene, 2,6-bis|isocyanato|toluene, 2,4-/2,6-bis|isocyanato|toluene and bis|4-isocyanatophenyl|methane.

5. A polymer according to claim 1 in which the tertiary phosphine groups in the 1,2-, 1,3-, 1,4- or 1,5-position are bonded to an aliphatic radical having a total of 4 to 12 C atoms, a cycloaliphatic radical having 3 to 8 C atoms, a heterocycloaliphatic radical having 2-6 C atoms in the heterocyclic moiety, an aromatic radical having 6 to 20 C atoms or a heteroaromatic radical having 2 to 12 C atoms in the heterocyclic moiety.

6. A polymer according to claim 1, wherein the diphosphine is a compound of the formula Ia or Ib

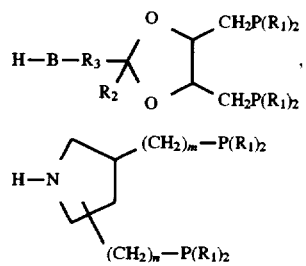

in which
the $R_1$ are identical or different radicals and independently of one another are $C_1$-$C_{12}$alkyl, $C_5$-$C_{12}$cycloalkyl, phenyl, $C_5$-$C_{12}$cycloalkyl which is substituted by $C_1$-$C_4$alkyl or $C_1$-$C_4$alkoxy or phenyl which is mono- to trisubstituted by $C_1$-$C_4$alkyl, $C_1$-$C_4$alkoxy, $C_1$-$C_4$halogenalkyl, —$SiR_4R_5R_6$, halogen, —$SO_3M$, —$CO_2M$, —$PO_3M$, —$NR_7R_8$ or —|$^+NR_7R_8R_9$|$X^-$;
or the two $R_1$ of a group $(R_1)_2P$ together are o,o'-diphenylene;
$R_2$ is hydrogen, linear or branched $C_1$-$C_{12}$alkyl, phenyl or benzyl;
$R_3$ is $C_1$-$C_{12}$alkylene;
the groups $(R_1)_2P(CH_2)_{m\ or\ n}$ are in the o- or m-position relative to one another;
B is —$NR_{10}$- or —O—;
$R_4$, $R_5$ and $R_6$ independently of one another are $C_1$-$C_{12}$alkyl or phenyl;
$R_7$ and $R_8$ are H, $C_1$-$C_{12}$alkyl or phenyl, or
$R_7$ and $R_8$ together are tetramethylene, pentamethylene or 3-oxa-1,5-pentylene;

$R_9$ is H or $C_1$-$C_4$alkyl;
M is H or an alkali metal;
$X^-$ is the anion of a monobasic acid;
$R_{10}$ is hydrogen or linear or branched $C_1$-$C_6$alkyl;
and m and n independently of one another are 0 or 1.

7. A polymer according to claim 6, in which $R_1$ in formula Ia or Ib are $C_1$-$C_8$alkyl.

8. A polymer according to claim 6, in which the cycloalkyl $R_1$ in formula Ia or Ib contains 5 to 8 ring C atoms.

9. A polymer according to claim 6, in which $R_1$ in formula Ia or Ib is phenyl, 2-methyl-, 3-methyl-, 4-methyl-, 2- or 4-ethyl-, 2- or 4-i-propyl-, 2- or 4-t-butyl-, 2-methoxy-, 3-methoxy-, 4-methoxy-, 2- or 4-ethoxy-, 4-trimethylsilyl-, 2- or 4-fluoro-, 2,4-difluoro-, 2- or 4-chloro-, 2,4-dichloro-, 2,4-dimethyl-, 3,5-dimethyl-, 2-methoxy-4-methyl-, 3,5-dimethyl-4-methoxy-, 3,5-dimethyl-4-(dimethylamino)-, 2- or 4-amino-, 2- or 4-methylamino-, 2- or 4-(dimethylamino)-, 2- or 4-$SO_3H$-, 2- or 4-$SO_3Na$-, 2- or 4-|$^+NH_3Cl$|-, 2,4,6-trimethylphen-1-yl or 3,4, 5-trimethylphen-1-yl, 4-trifluoromethylphenyl or 3,5-di(trifluoromethyl).

10. A polymer according to claim 6, in which the $R_1$ in formula Ia or Ib are identical radicals and are phenyl, cyclohexyl, t-butyl, 2- or 4-methylphen-1-yl, 2- or 4-methoxyphen-1-yl, 2- or 4-(dimethylamino)phen-1-yl, 3,5-dimethyl-4-(dimethylamino)phen-1-yl or 3,5-dimethyl-4-methoxyphen-1 -yl, 4-trifluoromethylphenyl or 3,5-di (trifluoromethyl).

11. A polymer according to claim 6, in which the $R_1$ in formula Ia or Ib are phenyl and m+n in formula Ib is 0, 1 or 2.

12. A polymer according to claim 6, in which, in formula Ib, $R_1$ is phenyl, m is 0 and n is 1 and the groups $(R_1)_2P$- and $(R_1)_2PCH_2$- are bonded in the m-position, or m and n are 0 and the groups $(R_1)_2P$- in the o-position.

13. A polymer according to claim 6, wherein the compounds of the formula Ia or Ib are present in the form of the optically active R,R-, S,S-, R,S- or S,R-isomers with respect to the position of the phosphine(methyl) groups.

14. A polymer according to claim 1, which is a non-crosslinked thermoplastic, crosslinked or structurally crosslinked polymer.

15. A polymer according to claim 1, which is an essentially non-crosslinked polymer which is soluble in organic solvents, a partly crosslinked swellable polymer or a highly crosslinked porous polymer.

16. A polymer according to claim 1, wherein the loading of the polymer with tertiary diphosphine groups in the 1,2-,1,3-,1,4- or 1,5-position is between 5 and 100 mol %, based on the available hydroxyl-, or primary or secondary amino group.

17. A polymer according to claim 1, wherein the monomers which form the polymer are chosen from the group consisting of styrene, p-methylstyrene or α-methylstyrene, at least one of which contains a bonded hydroxyl group or primary or secondary amino group as the functional group.

18. A polymer according to claim 17, wherein further comonomers of dienes or acrylic derivatives, for example butadiene, acrylonitrile, alkyl methacrylate, butadiene/alkyl acrylate and methacrylate, maleic anhydride or acrylonitrile/methyl acrylate which form random or block copolymers are present.

19. A polymer according to claim 1, wherein the monomers which form the polymer are chosen from the group consisting of α,β-unsaturated acids and esters or amides thereof, at least one of which contains a bonded hydroxyl group or primary or secondary amino group as the functional group.

20. A polymer according to claim 19, wherein the monomers which form the polymer are chosen from the group consisting of acrylates and $C_1$–$C_4$alkyl esters thereof, methacrylates and $C_1$–$C_4$alkyl esters thereof, acrylamide and acrylonitrile, at least one of which contains a bonded hydroxyl group or primary or secondary amino group as the functional group.

21. A polymer according to claim 20, wherein further olefinically unsaturated monomers which form random or block copolymers are present.

22. A polymer according to claim 1, wherein the polymer is formed from monomers which contain vinyl alcohol as a homopolymer or vinyl alcohol as a copolymer with vinyl acetate, stearate, benzoate or maleate, vinylbutyral, allyl phthalate or allylmelamine.

23. A polymer according to claim 1, wherein the monomers which form the polymer are phenol and a $C_1$–$C_4$aldehyde.

24. A polymer according to claim 1, wherein the monomers which form the polymer form a polyepoxide of cyclic $C_3$–$C_6$ethers or $C_2$–$C_6$alkylene glycols and bisglycidyl ethers.

25. A polymer according to claim 1, which is a polysaccharide.

26. A polymer according to claim 25, wherein the polysaccharide is cellulose, a cellulose acetate, propionate or butyrate, a cellulose ether, starch, chitin or chitosan.

27. A polymer according to claim 1, wherein the recurring structural elements of at least one monomer MM are a compound of the formula IIa, IIb, IIc or IId (IIa)

(IIb)

(IIc)

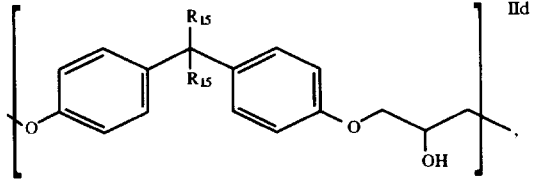

in which $R_{14}$ is $C_1$–$C_4$alkylene and $R_{11}$, $R_{12}$, $R_{13}$ and $R_{15}$ independently of one another are hydrogen or $C_1$–$C_4$alkyl.

28. A polymer according to claim 15, which is a highly crosslinked macroporous polystyrene or polyacrylate.

29. A polymer according to claim 15, wherein the particle size of the porous highly crosslinked polymer is 10 μm to 2000 μm.

30. A polymer according to claim 15, wherein the specific surface area of the porous highly crosslinked polymers is 5 to 1000 m².

31. A process for the preparation of a polymer according to claim 1, which comprises reacting the polymer which is soluble, swellable or insoluble in organic solvents and has recurring structural elements of at least one monomer MM which contains a hydroxyl group or a primary or secondary amino group bonded directly or in a side chain as a functional group, A) in a first step completely or partly with a diisocyanate which forms a bridge group Q in an inert organic solvent, and in a second step reacting the product completely or partly with an aliphatic, cycloaliphatic, heterocycloaliphatic, aromatic or heteroaromatic ditertiary diphosphine, the phosphine groups of which are bonded with a carbon chain in the 1,2-, 1,3-, 1,4- or 1,5-position relative to one another and which contains a hydroxyl group or a primary or secondary amino group; or B) in a first step, reacting an aliphatic, cycloaliphatic, heterocycloaliphatic, aromatic or heteroaromatic ditertiary diphosphine, the phosphine groups of which are bonded to a carbon chain in the 1,2-, 1,3-, 1,4- or 1,5-position relative to one another and which contains a hydroxyl group or a primary or secondary amino group, completely or partly with a diisocyanate which forms a bridge group Q in an inert organic solvent and, in a second step, reacting the product completely or partly with a polymer having recurring structural elements of at least one monomer MM which contains a bonded hydroxyl group or a primary or secondary amino group as a functional group; and C) crosslinking any free isocyanate groups with a $C_2$–$C_{24}$diol or $C_2$–$C_{24}$diamine or reacting them with a $C_2$–$C_{12}$alcohol or $C_2$–$C_{12}$amine.

* * * * *